(12) United States Patent
Contreras

(10) Patent No.: US 11,160,574 B2
(45) Date of Patent: Nov. 2, 2021

(54) NOSE CLEARING ASSEMBLY

(71) Applicant: Dave Contreras, El Paso, TX (US)

(72) Inventor: Dave Contreras, El Paso, TX (US)

(*) Notice: Subject to any disclaimer, the term of this patent is extended or adjusted under 35 U.S.C. 154(b) by 95 days.

(21) Appl. No.: 16/728,110

(22) Filed: Dec. 27, 2019

(65) Prior Publication Data

US 2021/0196297 A1    Jul. 1, 2021

(51) Int. Cl.
*A61B 17/24* (2006.01)

(52) U.S. Cl.
CPC ........ *A61B 17/24* (2013.01); *A61B 2017/246* (2013.01)

(58) Field of Classification Search
CPC ... A61B 17/24; A61B 2017/246; A61B 17/50; A61F 11/006; A61F 13/38; A61M 35/00
See application file for complete search history.

(56) References Cited

U.S. PATENT DOCUMENTS

| | | | |
|---|---|---|---|
| 4,962,607 A | 10/1990 | Baldwin | |
| 5,715,559 A | 2/1998 | Mitri | |
| 6,270,510 B1 | 8/2001 | Westendorf | |
| 8,551,031 B2 | 10/2013 | Edme | |
| 2003/0108846 A1* | 6/2003 | Hoertsch | B08B 1/003 433/216 |
| 2008/0086887 A1 | 4/2008 | Park | |
| 2015/0039003 A1 | 2/2015 | Wilson | |

* cited by examiner

*Primary Examiner* — Tan-Uyen T Ho
*Assistant Examiner* — Arwa Mostafa

(57) ABSTRACT

A nose clearing assembly for cleaning a user's nostrils includes a tube that is insertable into a nostril of user. A swab is coupled to the tube and the swab can be inserted into the user's nostril. The swab is comprised of a fluid absorbent material for absorbing fluid mucous from the user's nostril. A shovel is coupled to the tube and the shovel can be inserted into the user's nostril. The shovel lies on a plane that is oriented perpendicular to a longitudinal axis of the tube. In this way the shovel can engage, and subsequently remove, dried mucous from the user's nostril.

3 Claims, 3 Drawing Sheets

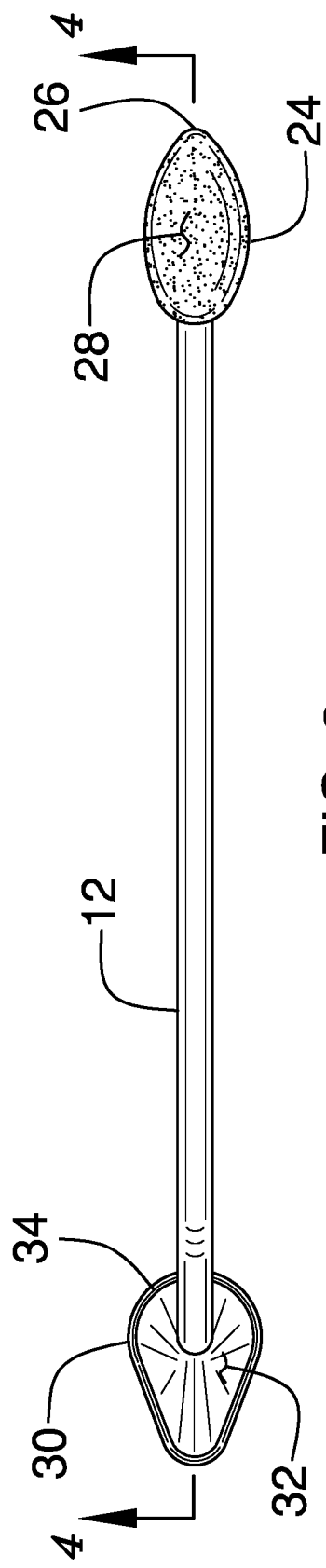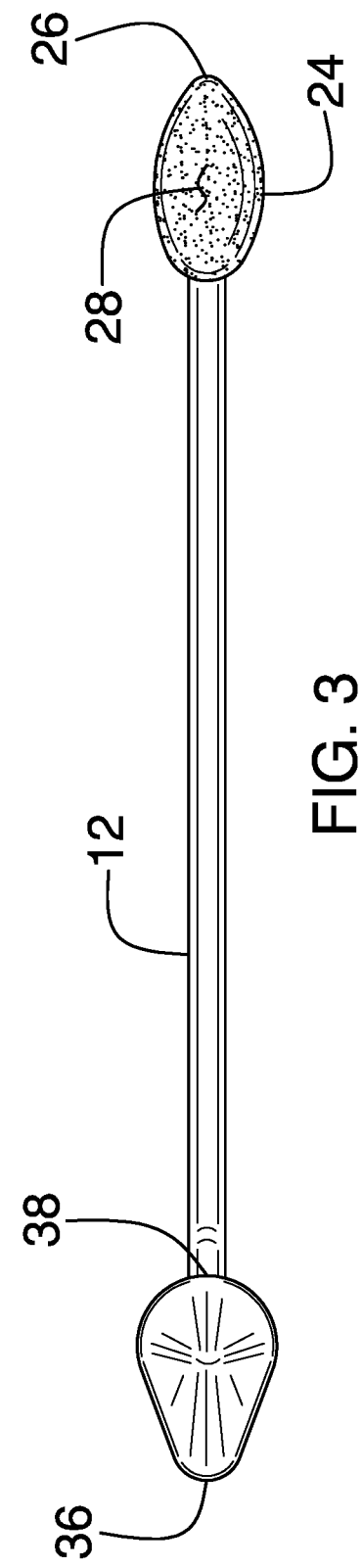

NOSE CLEARING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to nose clearing devices and more particularly pertains to a new nose clearing device for cleaning a user's nostrils.

(2) Description of Related Art Including Information Disclosed Under 37 CFR 1.97 and 1.98

The prior art relates to nose clearing devices. The prior art discloses a bore cleaning tool that includes a plurality of cleaning head, each with a plurality of flared edges, for cleaning a bore. The prior art discloses a variety of cleaning sticks which include a pair of cleaning pads for inserting into bodily openings. In each instance the pair of cleaning pads on the cleaning stick are similar to each other. In another instance the prior art discloses a cleaning stick with a pair of different cleaning ends, one comprising a pad and one comprising a closed loop. The prior art also discloses a variety of mechanized cleaning devices.

BRIEF SUMMARY OF THE INVENTION

An embodiment of the disclosure meets the needs presented above by generally comprising a tube that is insertable into a nostril of user. A swab is coupled to the tube and the swab can be inserted into the user's nostril. The swab is comprised of a fluid absorbent material for absorbing fluid mucous from the user's nostril. A shovel is coupled to the tube and the shovel can be inserted into the user's nostril. The shovel lies on a plane that is oriented perpendicular to a longitudinal axis of the tube. In this way the shovel can engage, and subsequently remove, dried mucous from the user's nostril.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 2 is a top view of an embodiment of the disclosure.

FIG. 3 is a bottom view of an embodiment of the disclosure.

DETAILED DESCRIPTION OF THE INVENTION

Figure 1:
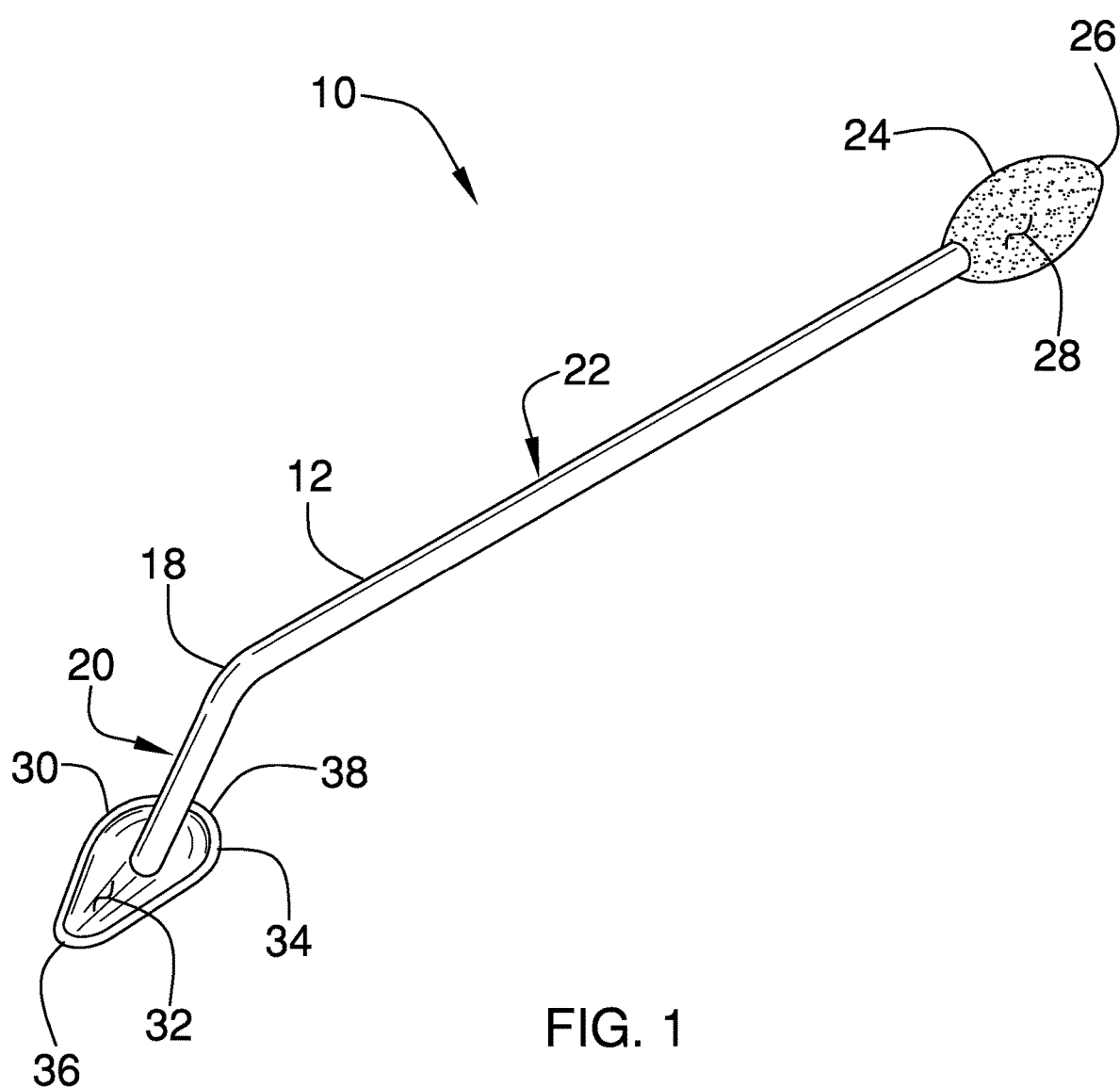
FIG. 1 is a top perspective view of a nose clearing assembly according to an embodiment of the disclosure.
Figure 4:
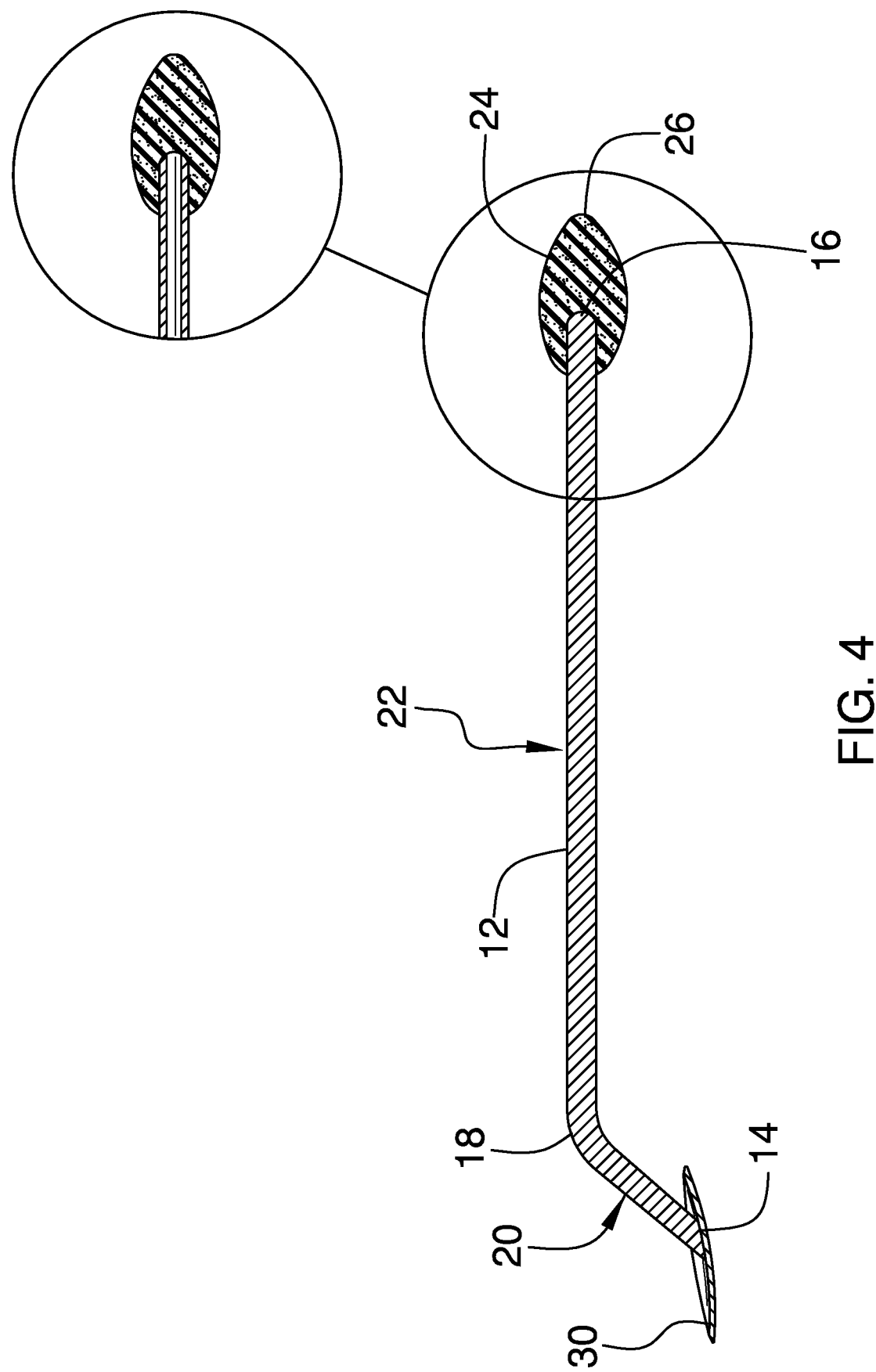
FIG. 4 is a cross sectional view taken along line 4-4 of FIG. 2 of an embodiment of the disclosure.

With reference now to the drawings, and in particular to FIGS. 1 through 4 thereof, a new nose clearing device embodying the principles and concepts of an embodiment of the disclosure and generally designated by the reference numeral 10 will be described.

As best illustrated in FIGS. 1 through 4, the nose clearing assembly 10 generally comprises a tube 12 that is insertable into a nostril of user. The tube 12 has a first end 14 and a second end 16, and the tube 12 has a bend 18 thereon to define a first portion 20 of the tube 12 forming an angle with a second portion 22 of the tube 12. The bend 18 is positioned closer to the first end 14 than the second end 16. The first portion 20 may have a length ranging between approximately 3.0 inches and 5.0 inches, and the second portion 22 may have a length ranging between approximately 0.5 inches and 1.0 inches.

A swab 24 is coupled to the tube 12 and the swab 24 can be inserted into the user's nostril. The swab 24 is comprised of a fluid absorbent material to absorb fluid mucous from the user's nostril. The swab 24 is positioned on the second end 16 of the tube 12 and the swab 24 has a distal end 26 with respect to the tube 12 and an outer surface 28. The swab 24 is elongated between the second end 16 and the distal end 26, and the outer surface 28 is continuously arcuate about a centerline of the swab 24 such that the swab 24 has an ovoid shape. The swab 24 may be comprised of foam rubber, cotton fiber, or any other absorbent material that is sufficiently soft for comfortably engaging the user's mucous membranes.

A shovel 30 is provided and the shovel 30 is coupled to the tube 12 for inserting into the user's nostril. The shovel 30 lies on a plane that is oriented perpendicular to a longitudinal axis of the tube 12. In this way the shovel 30 can engage, and subsequently remove, dried mucous from the user's nostril. The shovel 30 has a top surface 32 and a perimeter edge 34 extending therebetween. The top surface 32 is concavely arcuate with respect to the perimeter edge 34 such that the shovel 30 forms a bowl.

The top surface 32 is coupled to the first end 14 of the tube 12 and the first end 14 is centrally positioned on the top surface 32. The perimeter edge 34 curves around the first end 14 of the tube 12 such that the shovel 30 has an ovoid shape with a narrow end 36 and a wide end 38. The shovel 30 is oriented such that an axis extending between the narrow end 36 and the wide end 38 is oriented collinear with a longitudinal axis of the second portion 22 of the tube 12. In this way the narrow end 36 enhances engaging the dried mucous.

In use, the tube 12 is gripped and the swab 24 is inserted into the user's nostril to clean the nostril and to absorb fluid mucous in the nostril. In this way the user can clean their nostril without introducing bacteria from their fingers into their nostril. The shovel 30 can be inserted into the user's nostril to dislodge, a subsequently remove, dried mucous from the user's nostril. The shovel 30 facilitates the same benefit of the swab 24 with respect to limiting bacteria introduced to the nostril.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A nose clearing assembly being configured to swab a nostril or remove dried mucous from the nostril, said assembly comprising:
   a tube being insertable into a nostril of user; and
   wherein said tube has a first end and a second end, said tube having a bend thereon to define a first portion of said tube forming an angle with a second portion of said tube, said bend being positioned closer to said first end than said second end; and
   a swab being coupled to said tube wherein said swab is configured to be inserted into the user's nostril, said swab being comprised of a fluid absorbent material wherein said swab is configured to absorb fluid mucous from the user's nostril; and
   a shovel being coupled to said tube wherein said shovel is configured to be inserted into the user's nostril, said shovel lying on a plane being oriented perpendicular to aft longitudinal axis of said first portion of said tube wherein said shovel is configured to engage, and subsequently remove, dried mucous from the user's nostril; and
   wherein said shovel has a top surface and a perimeter edge extending therebetween, said top surface being concavely arcuate with respect to said perimeter edge such that said shovel forms a bowl, said top surface being coupled to said first end of said tube, said first end being centrally positioned on said top surface; and
   wherein said perimeter edge curves around said first end of said tube such that said shovel has an ovoid shape having a narrow end and a wide end, said shovel being oriented such that an axis extending between said narrow end and said wide end is oriented collinear with a longitudinal axis of said second portion of said tube wherein said narrow end is configured to enhance engaging the dried mucous.

2. The assembly according to claim 1, wherein said swab is positioned on said second end of said tube, said swab having a distal end with respect to said tube and an outer surface, said swab being elongated between said second end and said distal end, said outer surface being continuously arcuate about a centerline of said swab such that said swab has an ovoid shape.

3. A nose clearing assembly being configured to swab a nostril or remove dried mucous from the nostril, said assembly comprising:
   a tube being insertable into a nostril of user, said tube having a first end and a second end, said tube having a bend thereon to define a first portion of said tube forming an angle with a second portion of said tube, said bend being positioned closer to said first end than said second end;
   a swab being coupled to said tube wherein said swab is configured to be inserted into the user's nostril, said swab being comprised of a fluid absorbent material wherein said swab is configured to absorb fluid mucous from the user's nostril, said swab being positioned on said second end of said tube, said swab having a distal end with respect to said tube and an outer surface, said swab being elongated between said second end and said distal end, said outer surface being continuously arcuate about a centerline of said swab such that said swab has an ovoid shape; and
   a shovel being coupled to said tube wherein said shovel is configured to be inserted into the user's nostril, said shovel lying on a plane being oriented perpendicular to a longitudinal axis of said first portion of said tube wherein said shovel is configured to engage, and subsequently remove, dried mucous from the user's nostril, said shovel having a top surface and a perimeter edge extending therebetween, said top surface being concavely arcuate with respect to said perimeter edge such that said shovel forms a bowl, said top surface being coupled to said first end of said tube, said first end being centrally positioned on said top surface, said perimeter edge curving around said first end of said tube such that said shovel has an ovoid shape having a narrow end and a wide end, said shovel being oriented such that an axis extending between said narrow end and said wide end is oriented collinear with a longitudinal axis of said second portion of said tube wherein said narrow end is configured to enhance engaging the dried mucous.

\* \* \* \* \*